(12) United States Patent
Leidl et al.

(10) Patent No.: US 6,774,645 B1
(45) Date of Patent: Aug. 10, 2004

(54) DEVICE AND METHOD FOR DETECTING DEPOSIT FORMATIONS ON SENSOR SURFACES WHERE LUBRICANTS CAUSE THE FORMATIONS

(75) Inventors: Anton Leidl, Munich, DE (US); Peter Langer, Munich (DE); Ulrich Virnich, Berg (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/168,457

(22) PCT Filed: Jan. 24, 2000

(86) PCT No.: PCT/EP00/00524

§ 371 (c)(1),
(2), (4) Date: Oct. 9, 2002

(87) PCT Pub. No.: WO01/55718

PCT Pub. Date: Aug. 2, 2001

(51) Int. Cl.[7] .............................................. G01R 27/26
(52) U.S. Cl. ....................................... 324/698; 324/658
(58) Field of Search .................... 73/10, 116; 324/439, 324/698, 658

(56) References Cited

U.S. PATENT DOCUMENTS

| | | | | |
|---|---|---|---|---|
| 4,646,070 A | * | 2/1987 | Yasuhara et al. | 340/603 |
| 5,071,527 A | * | 12/1991 | Kauffman | 205/786 |
| 5,604,441 A | * | 2/1997 | Freese, V et al. | 324/663 |
| 5,644,239 A | * | 7/1997 | Huang et al. | 324/439 |
| 5,824,889 A | * | 10/1998 | Park et al. | 73/116 |

* cited by examiner

Primary Examiner—Jay Patidar
Assistant Examiner—Walter Benson
(74) Attorney, Agent, or Firm—Beyer Weaver & Thomas LLP

(57) ABSTRACT

A device for determining whether a lubricant to be examined effects the formation of a deposit on a sensor element has a sensor element for detecting values of at least one physical parameter of the lubricant. The sensor element is in contact with the lubricant. Furthermore, there is provided a potential difference source for applying a potential difference between the sensor element and the lubricant. Moreover, there is provided an evaluator for evaluating at least two values of the physical parameter which are detected at different potential states between the sensor element and the lubricant in order to thus determine whether the lubricant causes a deposit formation on the sensor element.

12 Claims, 2 Drawing Sheets

DEVICE AND METHOD FOR DETECTING DEPOSIT FORMATIONS ON SENSOR SURFACES WHERE LUBRICANTS CAUSE THE FORMATIONS

BACKGROUND OF THE INVENTION

1. Field of the Invention

The present invention relates to a device and a method for detecting deposition formations on sensor surfaces, which are caused by lubricants. In particular, the present invention relates to such a device and such a method that are suited to be utilized in determining the aging condition of lubricants, in particular lubricating oils used in internal combustion engines. In addition thereto, the present invention relates in particular to such a device and such a method that are suitable for eliminating deposits formed on sensor surfaces. The present invention thus is suited in particular for an "in situ" detection of the aging conditions of lubricating oils so that, on the basis of such a detection, oil changing intervals may be determined.

2. Description of Prior Art

Lubricating oils, in particular lubricating oils in internal combustion engines, are changed as a rule in fixed time intervals. So far, there are no reliable sensor systems available that are capable of reliably determining the condition, i.e. the aging condition, of a lubricating oil while the lubricating oil is within the engine. There is a number of different sensor systems known that detect various parameters in order to determine the aging condition of the oil on the basis of the parameters detected.

For example, the document DE 4131969 C2 reveals a lubricating oil monitoring means in which the parameters pressure, temperature and viscosity and optionally the pH value are detected in situ in the engine. On the basis of the parameters ascertained, an actual condition of the engine oil is determined. This actual condition is compared to a desired condition and, if the desired condition shows a specific deviation with respect to the actual condition, an alarm signal is output indicating that an oil change is necessary. According to said DE 4131969 C2, the pressure is measured by means of a pressure sensor membrane provided with piezoresistive resistors, the temperature is measured by means of platinum resistors, the pH value is measured by means of a MOS transistor having an $H^+$-sensitive gate electrode, while the viscosity is measured from the relative permittivity, ascertained by means of capacitance structures, or alternatively from the attenuation of sound waves generated by piezo oscillators.

The document WO 98/05953 reveals a surface-wave liquid sensor comprising a transmitting transducer and a receiving transducer constituted by respective interdigital transducers. The number of finger pairs of the interdigital transducers as well as the material of which the electrodes are made are selected such that the volume shear wave generated by the transmitting transducer and the surface shear wave generated by the transmitting transducer have different frequencies.

In addition thereto, the document WO 98/37412 reveals a sensor means for detecting material parameters of a liquid medium, in which a surface-wave liquid sensor is used for detecting the viscosity of an adjacent liquid medium, while one of the interdigital transducers of the surface-wave liquid sensor is used furthermore for determining the relative permittivity of the adjacent liquid medium. Moreover, this document teaches to detect as an additional parameter the conductivity by way of the complex electrical impedance of the interdigital capacitor. On the basis of the parameters thus ascertained, there is determined, in consideration of the temperature dependency, an actual condition of the liquid medium which is compared to a desired condition in order to be thus able to determine an aging condition of the liquid medium, in particular of the lubricating oil.

The known oil condition sensors described hereinbefore thus permit the detection of viscosity, relative permittivity and conductivity of oils in situ in the engine. In this regard, the detection of the viscosity permits a more reliable determination of the condition of the oils than is possible using a mere dielectric measurement. However, the viscosity is a measurement quantity which in practical application is presently determined and evaluated mainly in laboratory analyses of engine oils. In such laboratory analyses, there are determined in addition to the viscosity among other things also the solids contents by means of infrared spectroscopy, as well as the acidification of the oil by determination of the TAN (TAN=total acid number). The oil condition is then assessed in the laboratory on the basis of these parameters.

On the engine test bench, i.e. in measuring the oil condition while the latter is within the engine, the use of surface-wave sensors as described hereinbefore has revealed that these, though permitting the in-situ detection of viscosity, yielded less reliable results. In addition thereto, it is to be pointed out that the methods that can be performed in laboratory analyses for reliably determining the oil condition cannot be employed for an examination of the oil within the motor due to the expenditure thereof.

SUMMARY OF THE INVENTION

It is the object of the present invention to provide a simple device and a simple method permitting a reliable determination of the aging condition of lubricating oils.

According to a first aspect of the present invention this object is achieved by a device for determining whether a lubricant to be examined causes the formation of a deposit on a sensor, comprising a sensor element for detecting values of at least one physical parameter of the lubricant, said sensor element being arranged in contact with the lubricant. Furthermore, there is provided a potential difference source for applying a potential difference between the sensor element and the lubricant. Moreover, the device according to the invention comprises an evaluator for evaluating at least two values of the physical parameter that are detected at different potential states between sensor element and lubricant, in order to thus determine whether the lubricant causes a deposit formation on the sensor surface.

According to a second aspect of the present invention the above object is achieved by a method of determining whether a lubricant to be examined effects the formation of a deposit on a sensor element for detecting values of at least one physical parameter of the lubricant, said sensor element being arranged in contact with the lubricant, comprising the steps of:

generating different potential states between the sensor element and the lubricant and detecting the value of the physical parameter in at least two different potential states;

determining whether the lubricant causes the formation of a deposit on the sensor element, on the basis of the at least two detected values of the physical parameter.

The present invention is based on the finding that the use of sensor elements for detecting physical parameters of lubricants may be accompanied by a deposit formation on the sensor element, in particular the sensor surface thereof in contact with the lubricant. Such a deposit formation was noted in measurements on the engine test bench by means of a surface-wave sensor, but not in measurements in the laboratory that were carried out using the same lubricant samples, i.e. oil samples. It has been found out now that this deposit formation is caused by a potential difference between engine block/engine oil and sensor element. This deposit formation on the surface of the sensor exposed to the lubricant or oil, however, strongly impairs the measurement of the physical parameters of the oil, for example the viscosity and the relative permittivity of the same.

Such a deposit formation on the sensor surface may be caused by a potential difference inherently present between engine block/engine oil and sensor. However, the deposit formation interferes with the detection of a physical parameter of the oil by a corresponding sensor, since such a deposit falsifies the output signals of the sensor. By application of an electric potential of defined polarity between sensor and lubricant for a short period of time, which is in the range of a few minutes, it is possible now to effect an additional deposit formation. By application of a potential of opposite polarity, it is possible to remove the deposit again. It is to be noted in this regard that it has been found out that this deposit formation and deposit removal occurs in case of aged lubricants only, whereas a deposit formation does not take place with new lubricants. The reason therefor resides in the fact that the deposit is due to substances contained therein, in particular solids such as soot and the like, which are contained increasingly in the lubricant with increasing aging of the same and which have an electric charge, so that a deposit formation is achieved by application of a predetermined polarity between lubricant and sensor element, while the application of an opposite polarity effects the removal of a deposit present on the sensor element.

The present invention takes advantage of the effect described hereinbefore for determining whether a deposit formation is caused by an aged lubricant on a sensor element, by detecting at least two values of a physical parameter of the lubricant by means of a sensor element in the presence of two different potential states between sensor element and lubricant. On the basis of this determination, the aging of the lubricant can then be determined directly since, as elucidated hereinbefore, the deposit formation is dependent on the aging condition of the lubricant or oil under examination. On the other hand, it is possible according to the invention to take advantage of the aforementioned effect for eliminating a deposit formed on a sensor element, i.e. on the sensor surface thereof in contact with the lubricant, and to then carry out a non-falsified detection of physical parameters of the lubricant, for example the viscosity, the relative permittivity or the conductivity thereof.

In other words, it is possible according to the invention by purposeful application of a potential difference between sensor and lubricant or oil, to measure a sum parameter for the solids contents of the lubricant by means of a sensor that is responsive to changes of the physical boundary conditions at the sensor-lubricant interface. The deposit caused by application of the potential difference can be removed again by application of a potential difference of opposite polarity. After the sensor has been freed from the deposit, a sensor capable of measuring viscosities and/or dielectric quantities and being the same sensor as that used for determining the deposit formation, may be utilized for determining the viscosity and/or the dielectric oil properties.

The present invention thus renders possible a reliable determination of the oil condition.

In addition to the parameters ascertained so far for assessing the aging condition of an oil in situ in an engine, for example relative permittivity, conductivity, viscosity and the like, it is possible with the present invention to determine an additional sum parameter permitting a statement to be made on the aging condition of the oil, namely, as pointed out hereinbefore, the parameter whether the lubricating oil causes a deposit formation on a sensor element. This deposit formation may be dependent on various factors occurring with increasing aging of the lubricating oil, in particular the introduction of soot and other electrically charged solids into the lubricant or oil. In contrast thereto, other parameters, for example the relative permittivity and the conductivity, are also influenced in particular by other changes of the lubricant with increasing aging, such as e.g. the introduction of liquid substances, such as water or fuel, and chemical compounds that may cause thermal oxidation or acidification. The more of these alterations of the lubricant may be detected, the more reliable the assessment of the aging state of the lubricant.

In addition to the detection of an additional sum parameter, namely the deposit formation on a sensor surface by a lubricant, the present invention on the other hand permits the purposeful formation and removal of a deposit, respectively, so that the physical parameters of the lubricant, such as e.g. the relative permittivity, the conductivity or the viscosity, can be detected in a state in which the sensor is free from a deposit. Thus, in addition to the detection of an additional sum parameter, the present invention also renders possible a more accurate detection of the afore-mentioned physical parameters.

BRIEF DESCRIPTION OF THE DRAWINGS

Preferred embodiments of the present invention will be elucidated in more detail hereinafter with reference to the accompanying drawings, in which.

DESCRIPTION OF PREFERRED EMBODIMENTS OF THE INVENTION

Figure 1:
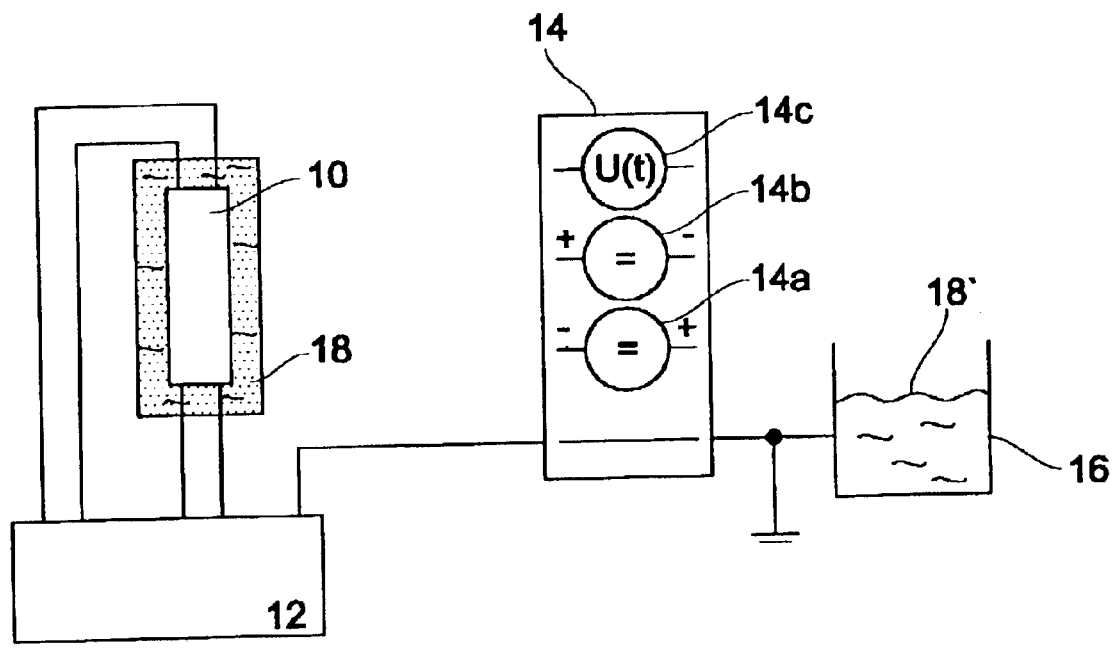
FIG. 1 shows a schematic view of a device according to the invention, for determining whether a lubricant to be examined causes the formation of a deposit on a sensor element.

FIG. 1 schematically illustrates a sensor element 10 which may be a conventional sensor element for detecting physical parameters of a lubricant, in particular a lubricating oil, for example a surface-wave sensor as described in documents WO98/05953 and WO98/37412. However, the sensor may be an arbitrary sensor for detecting physical parameters, with the output signal of said sensor being dependent on a liquid contacting the same, i.e. a sensor surface of the same, said liquid being in particular a lubricating oil. A preferred embodiment of such a sensor will be discussed in more detail hereinbelow with reference to FIG. 2. For example, a quartz oscillator as sensor element for detecting the viscosity, is conceivable in this respect as well.

Sensor 10 is connected to a sensor electronic unit 12 containing evaluation circuits for evaluating the output signals generated by sensor element 10. The sensor electronic unit 12, which in addition to the evaluation circuits also contains the control unit of the device according to the invention, is connected furthermore to a voltage source 14 that renders possible the application of a defined potential difference between an oil pan 16 and the sensor element 10. It is to be pointed out here that the oil pan 16 is named here in exemplary manner only; the potential difference between lubricating oil and sensor element may also be applied at a different location, for example between other parts of the engine block and the sensor element.

As shown in FIG. 1, the oil pan 16 may be considered to be at ground potential. FIG. 1 schematically illustrates furthermore part of the lubricant 18 that is in contact with the sensor element 10, in particular with a sensing surface, i.e. sensor surface, thereof. The voltage source 14 preferably is a controllable voltage source that permits the application of fixed potential differences of predetermined polarities 14a, 14b as well as the application of time-varying potential differences 14c between lubricant and sensor element.

It is to be pointed out with respect to FIG. 1 that the lubricant 18 shown is in fluid communication with the lubricant 18' contained in oil pan 16, so that the application of a voltage between oil pan 16 and sensor element 10 effects a potential difference to be present between lubricant 18 and sensor element 10. Thus, the device illustrated in FIG. 1 renders possible the application of different potential differences between sensor element 10 and lubricant 18 in order to permit conclusions to a deposit formation of the lubricant 18 on the sensor element 10 on the basis of the output signals of the sensor element 18 that are obtained with at least two different potential states, as will still be elucidated in more detail hereinbelow with reference to FIG. 3.

Figure 2:
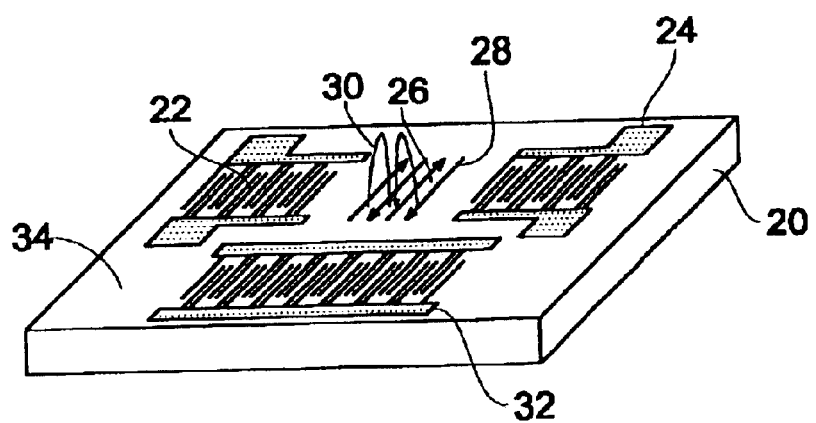
FIG. 2 shows a schematic view of a preferred embodiment of a sensor element used in the present invention.

However, at first a preferred embodiment of a sensor element will be elucidated in more detail by way of FIG. 2. The sensor element shown there comprises a quartz substrate 20 having two interdigital transducers 22, 24 arranged thereon in order to generate a surface wave, indicated by arrows 28, in a sensitive region 26. Moreover, FIG. 2 schematically illustrates an electric field 30. Furthermore, the quartz substrate 20 has an interdigital capacitor 32 arranged thereon. Such a sensor element as shown in FIG. 2 may be composed on the basis of the principles described in WO 98/05953 and WO 98/37412. The interdigital transducers 22, 24 there serve to detect the viscosity of a liquid present at the sensor surface 34, with the attenuation and frequency of the excited surface wave 28 being dependent on the adjoining liquid, in particular the viscosity thereof. For example, the attenuation of the excited surface wave 28 increases with increasing viscosity of the adjacent lubricating oil, whereas the frequency of the excited surface wave decreases with increasing viscosity of the adjacent lubricant. Furthermore, it is to be noted that the viscosity of the lubricant increases as a rule with increasing aging thereof.

The interdigital capacitor 32 serves to detect the dielectric constant and conductivity of the adjacent lubricant, respectively, with the conductivity and the dielectric constant or relative permittivity increasing as a rule with increasing aging condition of the lubricant. In addition to the interdigital capacitor described, there may also be other capacitive sensors employed according to the invention.

Differently from the sensor element shown in FIG. 2, it is also possible to employ a sensor element in which one of the interdigital transducers of the surface-wave sensor is used simultaneously as interdigital capacitor; in this regard, reference is made to the disclosure of WO 98/37412 as well. Furthermore, it is to be noted that, in addition thereto, temperature and pressure of the lubricant may be detected by suitable sensor means in order to be able to consider the particular dependencies of the detected physical parameter or parameters of the lubricant, for example the viscosity, the relative permittivity and the conductivity, on temperature and pressure in the assessment of the aging condition of the lubricant. Apart from the sensor element described with reference to FIG. 2, that serves for detecting viscosity, relative permittivity and conductivity, there may also be used other sensors that are responsive to changes of the physical boundary conditions at the sensor-lubricant interface.

It will be elucidated in the following with reference to FIG. 3 how an assessment can be made according to the invention as to whether a lubricant causes a deposit formation on a sensor element. This will be discussed in particular by way of the example of the detection of the viscosity of a lubricant using the device described with reference to FIGS. 1 and 2.

Figure 3:
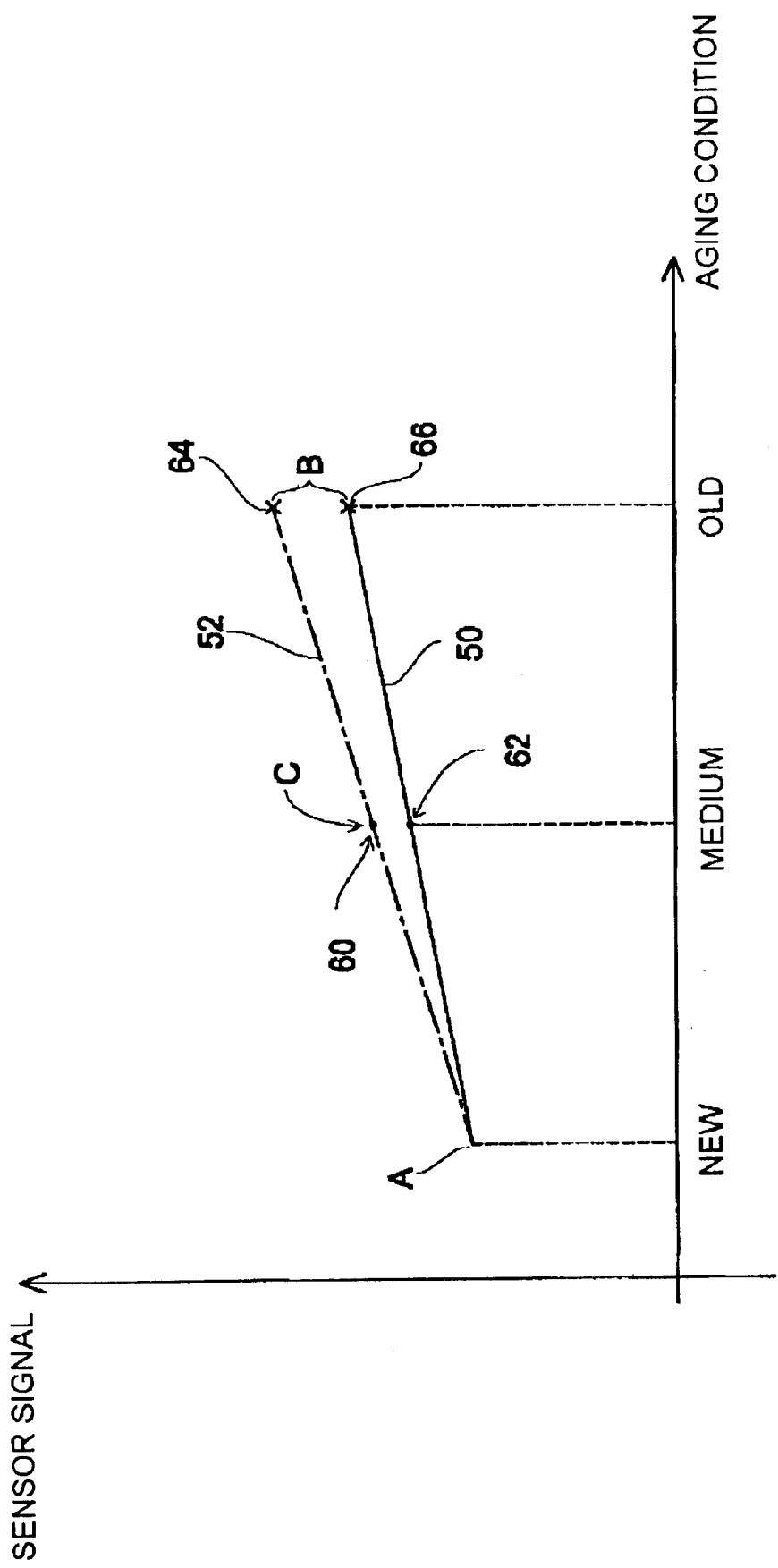
FIG. 3 shows a schematic view to illustrate the effect of a deposit formation that is advantageously used in the present invention.

FIG. 3 illustrates along the ordinate the sensor signal indicating the viscosity, whereas the abscissa depicts the aging condition which is subdivided merely schematically into new, medium and old. It is to be pointed out here that the illustration of FIG. 3 is merely of schematic nature, with the illustrated course of the viscosity being in no way matched to a natural course thereof. It is to be pointed out furthermore that the explanations given hereinafter, instead of with reference to the viscosity, could also be made with reference to another physical parameter, and it is to be noted furthermore that the evaluation can also take place using a parameter specific of a physical parameter of the respective lubricant under examination, for example the frequency of a surface wave that is specific for the viscosity of the lubricant. It is to be noted in this respect that the frequency of the surface wave decreases with increasing aging condition of the lubricant.

FIG. 3 illustrates by way of a curve 50 the course of the viscosity with increasing aging condition of the lubricant present at the sensor surface 34 (FIG. 2). As can be seen, the viscosity is increasing with increasing aging condition from "new" through "medium" to "old". Curve 50 depicts a viscosity detected by way of the frequency or the attenuation of a surface wave, without a deposit being present on the sensor element. In contrast thereto, the broken line 52 illustrates the course of the viscosity if there is a deposit present on the sensor surface, which is caused by the presence of a potential difference of a first polarity between sensor element and lubricant. As can be seen from FIG. 3, there is no deposit formation caused in case of a new lubricant, point A, whereas a deposit formation does take place in case of an aged lubricant, point B, which expresses itself in the form of an increase in viscosity. It is to be pointed out once more here that the course of the curves 50 and 52 is merely of schematic nature.

This deposit formation that is caused by aged lubricant can be detected now by the evaluation means in the sensor electronic unit 12. To this end, there are detected two values of the physical parameter, in the instant case the viscosity, at different potential states between sensor element and lubricant. Conceivable potential states in this regard are: no potential difference applied between sensor element and lubricant, positive potential difference applied between sensor element and lubricant (14b in FIG. 1), and negative potential difference applied between sensor element and lubricant (14a in FIG. 1). If different output signals of the sensor element are generated when different potential states are applied between sensor element and lubricant, this is an indication to the effect that the sensor surface is in contact with a lubricant that causes the formation of a deposit, i.e. that the lubricant has an advanced aging condition.

Thus, the evaluation of the two values detected allows the conclusion that a deposit formation is caused on the sensor element, and on the basis of this deposit formation in turn, it is possible to judge the aging condition of the lubricant.

As a preferred embodiment of the present invention, a case shall be elucidated herein in which a first potential difference of a first polarity is generated for detecting a first value of the physical parameter, and a second potential difference of a second polarity is generated for detecting the second value thereof. The second polarity is opposite to the first polarity. Furthermore, it is assumed that the first polarity causes a deposit formation on the sensor surfaces as shown in FIG. 3.

If the two values are being detected while a fresh lubricant is in contact with the sensor surface, one is in each case at point A, so that no difference appears between the two values. This indicates that no deposit formation is caused, so that it may be concluded therefrom that a new lubricant is involved.

If, in contrast thereto, a lubricant of medium aging condition is in contact with the sensor surface, one is in region C (FIG. 3), with the detection of the first value yielding a value 60 and the detection of the second value yielding a value 62. This is due to the fact that, by application of the potential difference of the first polarity, a deposit is formed first, which then is removed again by application of the potential difference of the second polarity. The difference between the values 60 and 62 indicates that a deposit formation takes place on the sensor element, with the amount of the difference allowing to infer therefrom the particular aging condition of the lubricant.

If an old lubricant is in contact with the sensor surface, a difference B results in comparable manner between the first value 64 detected and the second value 66 detected. It is thus possible to conclude therefrom a stronger deposit formation and thus an advanced aging condition of the lubricating oil.

It is pointed out that a result comparable to the above result is also obtained if the polarities of the potential differences applied are opposite; in this case, the value 62 would first be detected for a lubricant of medium aging condition, and the value 66 would first be detected in case of an "old" lubricant.

It has been assumed hereinbefore that there was no deposit present on the sensor surface when the first value was detected. However, the statements made hereinbefore apply analogously also in the event when there was a deposit present on the sensor surface when the first value was detected. In case of a sensor installed in an engine, such a deposit can be produced by a potential difference that is inherently present between engine oil and sensor and is not applied externally. In this case, too, there will be a deposit present on the sensor element when there is a potential state of one polarity present, whereas there will be no deposit present when a potential state of the other polarity is present. Thus, it is possible here, too, to draw conclusions therefrom as to the formation of a deposit being caused and to thus infer therefrom the aging condition of the lubricant.

In the example described hereinbefore for detecting the viscosity, the greater one of the values detected each time constitutes the value that indicates the presence of a deposit on the sensor element. It is thus possible to determine from this value the polarity of a potential difference that causes the formation of a deposit on the sensor element. By application of a potential difference of opposite polarity, the deposit can be removed from the sensor element.

Upon elimination of the deposit by application of the potential difference of opposite polarity, physical parameters, in the instant example the viscosity, of the lubricant to be examined can then be detected by means of the sensor element, with this detection being not falsified by any deposits on the sensor element. Thus, the present invention on the one hand permits the detection of an additional sum parameter, namely the deposit formation, and on the other hand a more accurate detection of physical parameters which have already been detected using conventional sensors, for example the viscosity, the relative permittivity, the conductivity and the like.

Although the detection of the viscosity as physical parameter has been elucidated hereinbefore with reference to FIG. 3, this explanation has general validity also for the detection of the conductivity and the relative permittivity and the like; in each case, one has to focus on the fact whether the respective physical parameter detected is increased or decreased by a deposit formation. It is to be noted in this regard that the conductivity and relative permittivity detected in the presence of a deposit are also higher or lower than in the case where no deposit is present.

It is to be pointed out that the intensity of the potential applied is of no relevance according to the invention, however, it being obvious to an expert that a potential difference of sufficient amount is to be applied in order to attract the particles contained in the lubricant to the sensor element. In like manner, it is obvious that the particular potential difference is to be applied for a suitable period of time, for example several minutes, so as to permit the formation and elimination of the deposit, respectively.

The period of time for which a potential difference is to be applied to effect complete elimination of the deposit can be detected, for example, by monitoring the output signals of the sensor element for a predetermined period of time during application of the potential difference effecting decomposition of the deposit. As of a certain moment of time, saturation will be reached, i.e. the output signal of the sensor represents exclusively the value of the physical parameter, without a deposit being present. The period of time up to this saturation value may then be used as suitable period of time. It is to be noted here that this duration may be reduced, for example, if the potential difference applied is increased.

The present invention thus is suited to find out whether a lubricant causes a deposit formation on a sensor element. This finding may then be used to determine the aging condition of the oil. Furthermore, this determination may be used to ensure the elimination of a deposit from the sensor element. The sensor free from the deposit may then be utilized for exactly detecting one or more physical parameters of the lubricating oil by means of the sensor element.

The present invention renders possible furthermore an observation of the aging of a lubricating oil over a period of time, for example several months or years, by detecting the physical parameter or parameters in each case with deposit formed on the sensor element and without deposit. The detection of such a development over time allows reliable statements to be made on the aging condition of the lubricant, in particular if actually alike lubricants in the fresh or new state thereof display deviations in the physical parameters. Such deviations may be compensated by comparing respective actual detected values of the physical parameter with desired values thereof which are detected as being descriptive of the new lubricant at the beginning of the use of the lubricant, for example after an oil change.

According to the invention, there are preferably two potential states employed, defining potential differences of different sign. However, it is also possible that a potential state does not define a potential difference between lubricant and sensor element. In addition thereto, the potential states may also define potential differences of the same sign and different extent, and in this case, the time behavior of the build-up of a deposit formation may then be utilized as additional factor for assessing a deposit formation.

The present invention thus provides a device and a method which, on the basis of the detection whether a lubricant causes a deposit formation on a sensor element, render possible a reliable determination of the aging condition of lubricants, in particular oils; on the basis of the determination of the aging condition, an oil change may then be carried out at the appropriate time. Thus, it is possible by means of the present invention to prevent on the one hand damaging of the engine by prolonged use of a spent oil, and to prevent on the other hand a premature oil change, so that unnecessary environmental pollution can be counteracted.

What is claimed is:

1. A device for determining whether a lubricant to be examined causes the formation of a deposit an a sensor element, comprising:
    a sensor element for detecting values of at least one physical parameter of the lubricant, said sensor element being arranged in contact with the lubricant;
    a potential difference source for applying different potential differences between the sensor element and the lubricant; and
    an evaluator for evaluating at least two values of the physical parameter that are detected while different potential differences are applied between the sensor element and the lubricant by the potential difference source, in order to thus determine whether the lubricant causes a deposit formation an the sensor element.

2. A device according to claim 1 comprising a means for determining the aging condition of the lubricant responsive to said determination as to whether a deposit formation is caused.

3. A device according to claim 1 comprising a means for determining the sign of the polarity of a potential difference between the sensor element and the lubricant which causes a deposit formation by the lubricant on the sensor element, and a means for eliminating a deposit on the sensor element by application of a potential difference of a polarity of opposite sign to said determined sign between said sensor element and said lubricant.

4. A device according to claim 3, further comprising a means for determining the aging condition of the lubricant on the basis of a value of the physical parameter that is detected after elimination of a deposit from the sensor element.

5. A device according to claim 1, wherein the sensor element comprises at least one of a surface-wave sensor or a quartz oscillator for detecting the viscosity of the lubricant and a capacitive sensor for detecting the relative permittivity or the conductivity of the lubricant.

6. A device according to claim 1, wherein said potential difference source is a voltage source arranged to apply the potential difference between an engine block, in which the lubricant is arranged, and said sensor element.

7. A method of determining whether a lubricant to be examined effects the formation of a deposit an a sensor element for detecting values of at least one physical parameter of the lubricant, said sensor element being arranged in contact with the lubricant, comprising:
    different potential states between the sensor element and the lubricant by applying different potential differences between the sensor element and the lubricant and detecting the value of the physical parameter in at least two different potential states; and
    determining whether the lubricant causes the formation of a deposit on the sensor element, on the basis of the at least two detected values of the physical parameter.

8. A method according to claim 7, further comprising the step of determining the aging condition of the lubricant on the basis of the determination as to whether a deposit formation is caused.

9. A method according to claim 7, further comprising the steps of:
    determining the sign of the polarity of a potential difference between the sensor element and the lubricant which causes a deposit formation by the lubricant on the sensor element, and
    eliminating a deposit on the sensor element by application of a potential difference of a polarity of opposite sign to said determined sign between said sensor element and said lubricant.

10. A method according to claim 9, further comprising the step of determining the aging condition of the lubricant on the basis of a value of the physical parameter that is detected after elimination of a deposit from the sensor element.

11. A method according to claim 7, wherein the sensor element used is at least one of a surface-wave sensor or a quartz oscillator for detecting the viscosity of the lubricant and a capacitive sensor for detecting the relative permittivity or the conductivity of the lubricant.

12. A method according claim 7, wherein said different potential states are produced by application of a voltage between an engine block in which the lubricant is arranged, and said sensor element.

* * * * *